US00PP07856P

United States Patent [19]

Jessel, Jr.

[11] Patent Number: Plant 7,856

[45] Date of Patent: Apr. 14, 1992

[54] CARNATION PLANT NAMED 'CFPC TAPESTRY'

[75] Inventor: Walter H. Jessel, Jr., Salinas, Calif.

[73] Assignee: California Florida Plant Co., L.P., Salinas, Calif.

[21] Appl. No.: 580,256

[22] Filed: Sep. 10, 1990

[51] Int. Cl.[5] ..... A01H 5/00

[52] U.S. Cl. ..... Plt./73

[58] Field of Search ..... Plt./70, 73

[56] References Cited

U.S. PATENT DOCUMENTS

P.P. 5,435 8/1985 Baratta et al. ..... Plt. 73

*Primary Examiner*—Howard J. Locker

*Attorney, Agent, or Firm*—Christie, Parker & Hale

[57] ABSTRACT

A new and unusual carnation of red purple coloration.

1 Drawing Sheet

BACKGROUND OF THE INVENTION

Carnation varieties producing flowers of many different colors are well known. However, it is desirable to provide a new standard variety of carnation producing flowers having red purple coloration with little or no streaking.

The closest known variety to 'CFPC Tapestry' is its seed parent Vanessa. However, the variety differs from its parent in improved vase-life (nearly twice), resistance to splitting, improved flower form higher flower production and faster response (4 to 5 weeks earlier). In addition, unlike 'Vanessa', 'CFPC Tapestry' does not burn or discolor at the petal edge during exposure to hot temperatures and the flowers are larger, have more petals and the petals reflex less at maturity. The new variety also out produces its parent by a free branching habit and the flower petals show less white and pink streaking than Vanessa.

SUMMARY OF THE INVENTION

The present invention relates to a new and distinct variety of carnation plant which was originated by me in a controlled breeding program by my crossing as seed parent, the variety known as 'Vanessa' (varietal denomination 'Lonsico', U.S. Plant Pat. No. 5,446) and as pollen parent, the variety known as 'Tanga' (varietal denomination 'Lontarion') (U.S. Plant Pat. No. 5,435). The varietal denomination of this new carnation is 'CFPC Tapestry'.

Among the novel characteristics possessed by the new variety which distinguish it from its parents and all other varieties of which I am aware are its unusual coloration, resistance to splitting and high flower production, in a standard. Flowers of the new variety also have good vase-life.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows a typical specimen of the vegetative growth and flower of the new variety depicted in color as nearly true as it is reasonably possible to make the same in a color illustration of this character.

DESCRIPTION OF THE NEW VARIETY

The new variety, 'CFPC Tapestry', produces flowers of red purple coloring and good form and vase-life. 'CFPC Tapestry' is especially suitable for commercial cut flower production.

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Tapestry.

Classification:

*Botanical.*—*Dianthus caryophyllus.*

*Commercial.*—Carnation, standard disbud type.

Parentage:

*Female parent.*—'Vanessa'.

*Male parent.*—'Tanga'.

PLANT

Height: About 39 inches.

Growing habit: Herbaceous, semi-upright.

Blooming habit: Terminal as a disbud.

Blooming season: Year round.

Rooting time: About 20 days.

Mutation prone: No evidence to date.

Disease resistance: Unknown.

Temperature tolerance: Typical for carnation.

FOLIAGE

Color:

*Upper side.*—Near to 189A.

*Lower side.*—Same as upper side.

Size: About 8 inches long and about ⅝-inch wide at base of plant.

Quantity: Numerous.
Shape: Lanceolate.
Texture: Smooth.
Ribs: Central keel.
Arrangement: Bi-lateral along stem.
Stem: Green.

BUD

Shape: Oval.
Color: Near to 144A.
Length: About 1½ inches.
Diameter: About ½ to ⅝ inch.

CALYX

Number of lobes (sepals): About 5.
Length: About 1½ inches.
Width: About ½ to ⅝ inch.
Color:
*Outside.*—Near to 144A.
*Inside.*—Near to 142D.

BLOOM

Shape: Round, serrated at petal edge.
Size:
*Diameter average.*—About 3½ to 4 inches.
*Depth average.*—About 1½ inches.
Borne: Terminal as disbudded.
Color:
*General tonality.*—Red purple.
*Upper side.*—Near to from 71B to 71C.
*Lower side.*—Near to 71B.
*Center.*—Near to 71B.
*Outer petals.*—Near to 71B.
Permanence: Yes.
Keeping habit: 10 to 12 days.
Fragrance: Slight.

PETALS

Number: About 37 to 42.
Outer petals:
*Length.*—About 2¼ inches.
*Width.*—About 2 inches.
Texture: Smooth.
Form: Fan shaped.

REPRODUCTIVE ORGANS

Stamen:
*Number.*—About 6–8.
*Arrangement.*—Around the ovary.
Anthers:
*Number.*—About 6–8.
*Length.*—About ¼ to ⅓ inch.
*Color.*—Near to 19C.
Filaments:
*Length.*—About 1⅓ inches.
*Color.*—About 19C.
*Number.*—About 2.
*Length.*—About 1 to 1½ inches.
*Color.*—Style — near to 36C to pinkish white at maturity.
Stigma:
*Number.*—About 2.
*Color.*—White.
Fertility:
*Male.*—Poor.
*Female.*—Very fertile.
Ovary:
*Shape.*—Conical, ribbed.
*Color.*—Base — greenish white. Body — greenish yellow. Apex — tan.

I claim:

1. A new and distinct variety of carnation plant, substantially as shown and described, characterized particularly by flowers of attractive red purple coloration.

* * * * *

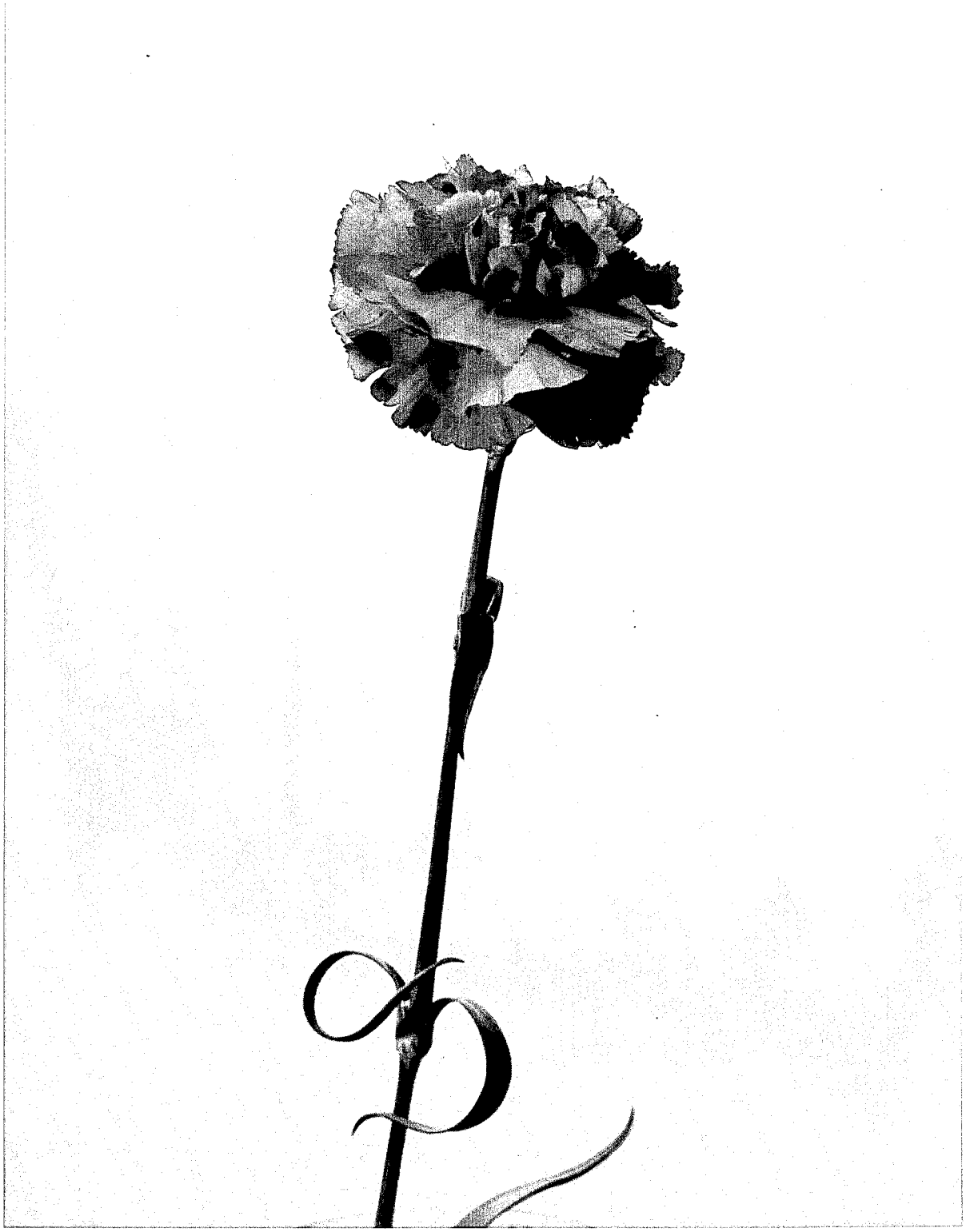

UNITED STATES PATENT AND TRADEMARK OFFICE

CERTIFICATE OF CORRECTION

PATENT NO. : Plant 7,856
DATED : April 14, 1992
INVENTOR(S) : Walter H. Jessel, Jr.

It is certified that error appears in the above-indentified patent and that said Letters Patent is hereby corrected as shown below:

On the title page, item [54] and in column 1, line 2, in the title , before "CARNATION" insert --NEW--.

Column 4, line 20, between the lines beginning with "Color" and "Number" insert --Pistil:--.

Signed and Sealed this

First Day of February, 1994

*Attest:*

*Attesting Officer*

Bruce Lehman

BRUCE LEHMAN

*Commissioner of Patents and Trademarks*